(12) United States Patent
Evans et al.

(10) Patent No.: US 8,343,082 B2
(45) Date of Patent: Jan. 1, 2013

(54) NONWOVEN SPLINTING AND CASTING PRODUCT

(75) Inventors: John C. Evans, NR Rochdale (GB); Shitij Chabba, Charlotte, NC (US); Martin O'Hara, Charlotte, NC (US)

(73) Assignee: BSN Medical, Inc., Charlotte, NC (US)

( * ) Notice: Subject to any disclaimer, the term of this patent is extended or adjusted under 35 U.S.C. 154(b) by 848 days.

(21) Appl. No.: 11/916,341

(22) PCT Filed: Jun. 2, 2006

(86) PCT No.: PCT/US2006/021438
§ 371 (c)(1),
(2), (4) Date: Jul. 22, 2008

(87) PCT Pub. No.: WO2006/132961
PCT Pub. Date: Dec. 14, 2006

(65) Prior Publication Data
US 2009/0216163 A1 Aug. 27, 2009

Related U.S. Application Data

(60) Provisional application No. 60/687,608, filed on Jun. 3, 2005.

(51) Int. Cl.
*A61F 5/00* (2006.01)

(52) U.S. Cl. .................................. 602/8; 602/5; 602/6

(58) Field of Classification Search .................. 602/5–9
See application file for complete search history.

(56) References Cited

U.S. PATENT DOCUMENTS

| 5,607,387 A | 3/1997 | Martin et al. |
| 2002/0035343 A1 | 3/2002 | Darcey |
| 2002/0160684 A1* | 10/2002 | Morris et al. ................. 442/415 |

* cited by examiner

*Primary Examiner* — Kim M Lewis

(74) *Attorney, Agent, or Firm* — Shumaker, Loop & Kendrick, LLP

(57) ABSTRACT

A medical bandaging product, including a non-woven, fibrous, flexible medical material adapted for being applied and conformed to a body part to be supported, and a reactive system impregnated into or coated onto the medical material. The system remains stable when maintained in a non-activated condition in the absence of an activating agent, such as water, and hardens upon activation by exposure to the activating agent to form a rigid, self supporting structure. An enclosure is provided within which the medical material is maintained against exposure to the activating agent until use. The product may be in pre-cut shapes or in roll-form for cutting off a desired length for a given use.

9 Claims, 14 Drawing Sheets

NONWOVEN SPLINTING AND CASTING PRODUCT

TECHNICAL FIELD AND BACKGROUND OF THE INVENTION

The present invention relates to medical bandage products. In particular, this invention relates to an orthopedic splinting product and a casting product, both utilizing a nonwoven substrate that can be used to stabilize a fracture or sprain or any other injury that requires a rigid or semi-rigid support.

Medical bandages for use in the treatment of injuries, such as broken bones requiring immobilization of a body member, are generally formed from a strip of fabric or scrim material impregnated with a substance which hardens into a rigid structure after the strip has been wrapped around the body member.

Conventional practice has been to fabricate a cast or splint upon an injured limb by initially applying to the limb a protective covering of a cotton fabric or the like, and then overwrapping the covering and limb with a substrate impregnated with plaster-of-paris or a substrate formed from flexible fiberglass fabric layers impregnated with a moisture-curable resin. Casts or splints formed from these materials possess several disadvantages. In particular, casts or splints formed using plaster-of-paris impregnated substrates have a relatively low strength to weight ratio. This results in a finished cast or splint that is very heavy and bulky. Furthermore, plaster-of-paris casts or splints are slow to harden, requiring 24 to 72 hours to reach maximum strength. Because plaster-of-paris breaks down in water, bathing and showering are difficult. Even if wetting due to these causes can be avoided, perspiration over an extended period of time can break down the plaster-of-paris and create a significant problem with odor and itching.

Casts or splints utilizing moisture-curable substrates formed from fiberglass fabric layers are lighter, waterproof and much stronger. However, cured casts or splints made using such substrates can become brittle, break down during wear which can lead to them being replaced. Furthermore, fiberglass is a composition that is highly irritating to mammalian skin.

In order to alleviate the above-recited disadvantages of the conventional cast or splint utilizing plaster-of-paris impregnated substrates and moisture-curable resin impregnated fiberglass substrates, resin-impregnated non-glass substrates formed from a knitted or woven fabric have been devised. The knitted fabric substrate provides a cast or splint that exhibits good conformability, possesses sufficient rigidity when cured, and shows no loss of strength. However, casting and splinting products incorporating knitted fabric substrates require a knitting process that is often expensive and time consuming. Additionally, casts and splints formed using a knitted fabric substrate can result in non-uniform and rough edges that are uncomfortable to the patient.

The present invention overcomes the disadvantages of the prior art by providing a substrate that does not irritate skin and is simple and inexpensive to manufacture.

SUMMARY OF THE INVENTION

Therefore, it is an object of the invention to provide initially flexible casting and splinting products that incorporate a nonwoven substrate.

It is another object of the invention to provide initially flexible casting and splinting products that incorporate a non-woven substrate having a uniform density.

It is another object of the invention to provide initially flexible casting and splinting products that have smooth, uniform edges when cured to a rigid or sem-rigid state.

It is another object of the invention to provide initially flexible casting and splinting products that are light weight and conformable.

According to one embodiment of the invention, a medical bandaging product is provided, comprising a non-woven, fibrous, flexible medical material adapted for being applied and conformed to a body part to be supported, and a reactive system impregnated into or coated onto the medical material. The system remains stable when maintained in a non-activated condition in the absence of an activating agent, and hardens upon activation by exposure to the activating agent to form a rigid, self supporting structure. An enclosure is provided within which the medical material is maintained against exposure to the activating agent until use.

According to another embodiment of the invention, the medical material comprises a cast tape, the reactive system comprises a reactive system that remains stable when maintained in substantially moisture-free conditions and hardens upon exposure to sufficient moisture to form a rigid, self supporting structure, and the activating agent comprises moisture.

According to yet another embodiment of the invention, the non-woven fibrous medical material is formed from fibers selected from the group consisting of glass, polyester, polypropylene and blends thereof.

According to yet another embodiment of the invention, the medical material is formed by a non-woven process selected from the group consisting of spray bonding, spun bonding, needle punching, felting, spun lacing, and stitch bonding.

According to yet another embodiment of the invention, the medical material has a weight of at least about 5 grams per square meter.

According to yet another embodiment of the invention, the non-woven medical material includes a reinforcement element selected from the group consisting of an inorganic filler, stitches, scrim, laminate, and plastic film.

According to yet another embodiment of the invention, the medical material is in a rolled configuration, and wherein the enclosure comprises an envelope.

According to yet another embodiment of the invention, a medical bandaging product is provided for being dispensed in predetermined lengths suitable for a given medical use, and comprises an elongate sleeve formed of moisture-impervious material and sealable to prevent entry of moisture, and an elongate medical material positioned in the sleeve and sealed therein against entry of moisture until use. The medical material comprises a substrate formed of a non-woven web, and a reactive system impregnated into or coated onto the non-woven substrate, the system remaining stable when maintained in substantially moisture-free conditions, and hardening upon exposure to sufficient moisture to form a rigid, self supporting structure. A soft, flexible protective cushion covering the substrate on at least one side along its length to provide a cushioning barrier between the substrate and the skin of a patient when the material is in use. Sealing means are provided for resealing the sleeve against entry of moisture after a predetermined length of the bandaging product has been dispensed for use to prevent hardening of the substrate remaining in the sleeve.

According to yet another embodiment of the invention, the non-woven medical material comprises fibers selected from the group consisting of glass, polyester, polypropylene and blends thereof.

According to yet another embodiment of the invention, the medical material is formed by a non-woven process selected from the group consisting of spray bonding, spun bonding, needle punching, felting, spun lacing, and stitch bonding.

According to yet another embodiment of the invention, the protective wrapping enclosing the substrate comprises a synthetic material, fibrous nonwoven cushion.

According to yet another embodiment of the invention, the protective wrapping enclosing the substrate comprises a nonwoven polypropylene tube.

According to yet another embodiment of the invention, the substrate comprises a single, uniform layer.

According to yet another embodiment of the invention, the medical bandaging product is positioned within a dispensing box.

According to yet another embodiment of the invention, the medical bandaging product is positioned within a dispensing box in a compact configuration of multiple overlaid lengths.

According to yet another embodiment of the invention, the configuration of multiple overlaid lengths comprises a coil.

According to yet another embodiment of the invention, a medical bandaging product is provided, comprising an enclosure sealable to prevent entry of moisture, and a medical material positioned in the sleeve in a substantially moisture-free condition and sealed therein against entry of moisture until use. The medical material comprises a non-woven substrate, a reactive system impregnated into or coated onto the substrate, the system remaining stable when maintained in substantially moisture-free conditions and hardening upon exposure to sufficient moisture to form a rigid, self supporting structure and comprising a blended polyisocyanate, polyol, catalyst and stabilizer; and a soft, flexible protective nonwoven web covering at least one major side of the substrate to provide a cushioning barrier between the substrate and the skin of a patient when the material is in use.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED
EMBODIMENT AND BEST MODE

Cast

Figure 1:
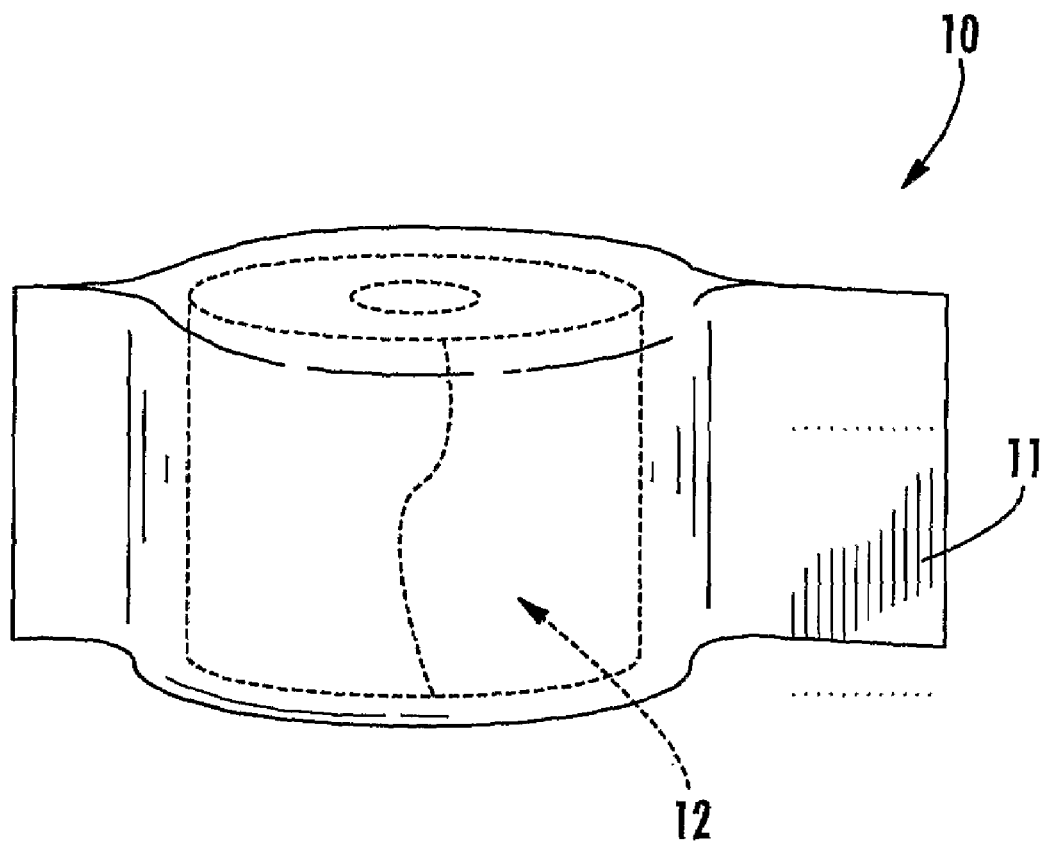
FIG. 1 shows a perspective view of a cast product including a moisture-proof storage package and a nonwoven medical cast bandage.

Referring now specifically to the drawings, a medical bandage product in the form of cast tape according to an embodiment of the invention is illustrated in FIG. 1 and shown generally at reference numeral 10. The medical bandage product 10 includes a moisture proof package, such as a pouch 11, in which is sealed a roll of flexible cast bandage 12. The bandage 12, coated or impregnated with a curable resin, remains in a flexible condition until the pouch is opened for use.

Figure 2:
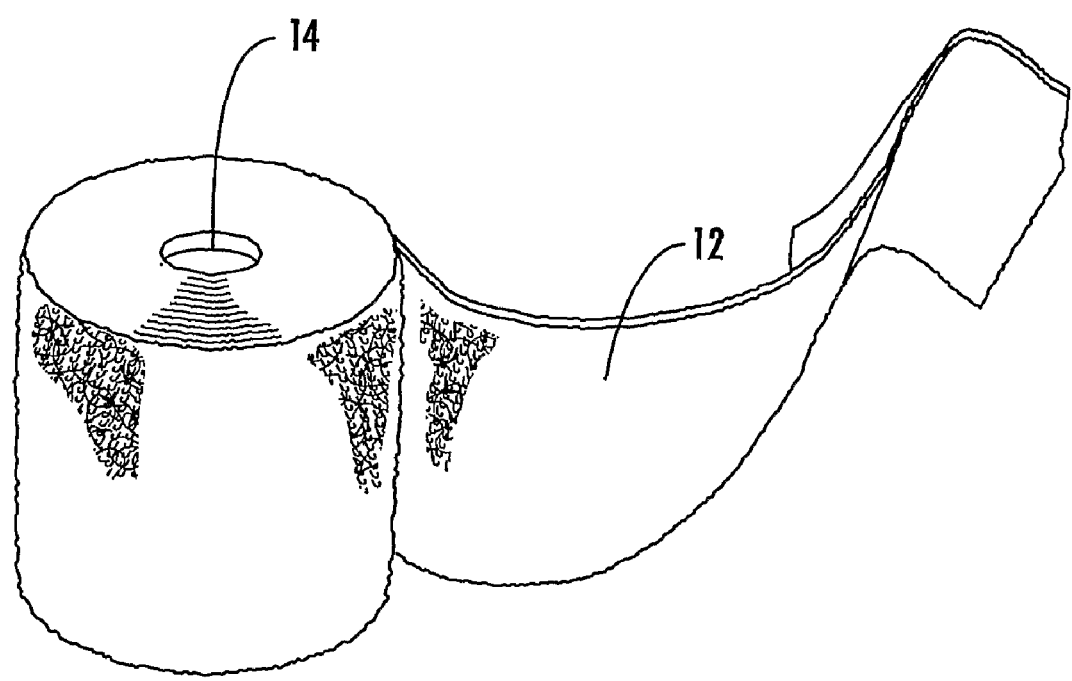
FIG. 2 is a perspective view of the nonwoven medical cast bandage according to an embodiment of the invention.
Figure 3:
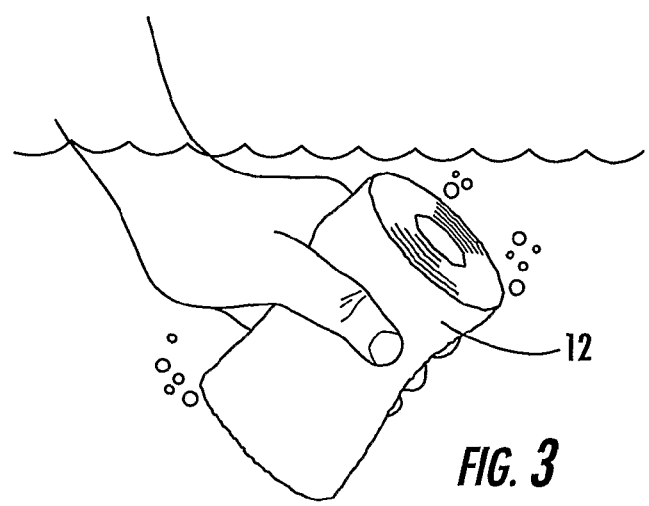
FIGS. 3-7 are sequential views of the steps by which the nonwoven cast bandage is prepared and applied to a lower leg.
Figure 4:
Figure 5:
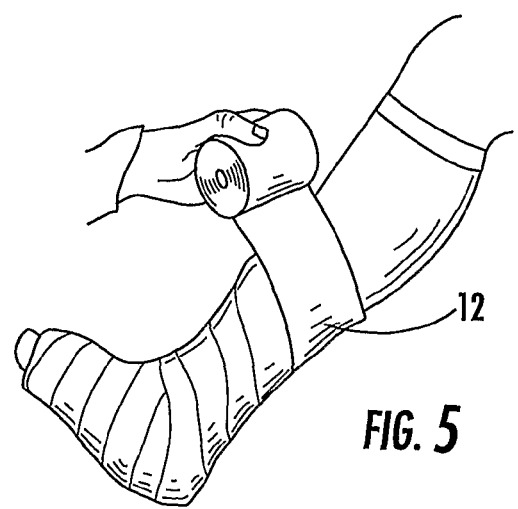
Figure 6:
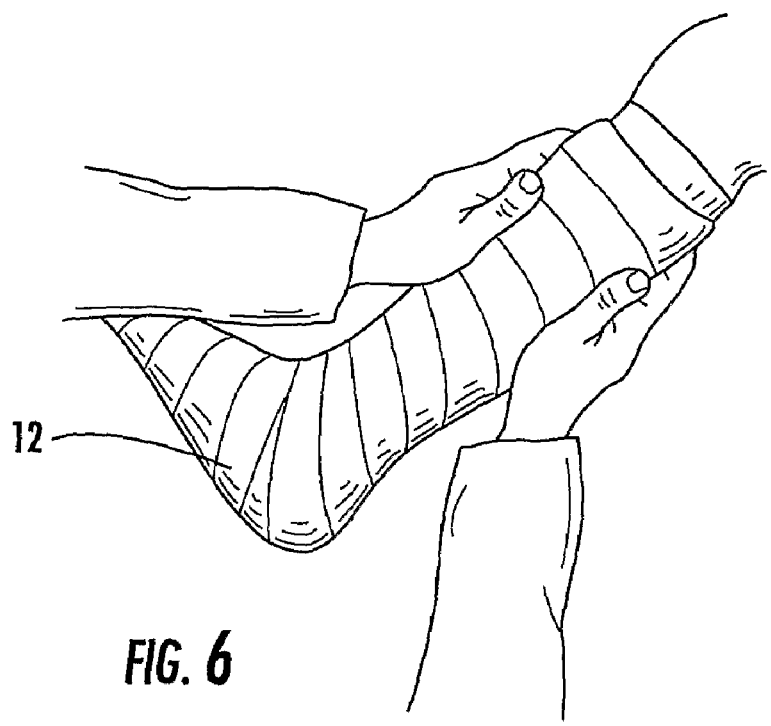

Referring now to FIG. 2, the bandage 12 is constructed using a known manufacturing technique, such as spray bonding, spun bonding, needle punching, felting, spun lacing, or stitch bonding. Bandage 12 may be constructed using any suitable organic or inorganic fibers. Examples of suitable fibers include glass, polyester, polypropylene and blends thereof.

The bandage 12 has a thickness suitable for use as a medical bandage. An example of a suitable thickness would be at least about 1 mm, and preferably between about 2 to about 8 mm. The bandage 12 may be designed so that it has a preferential stretch, strength, and other characteristics in one direction or, in the alternative, may be designed with the fibers laid randomly so that the bandage 12 exhibits uniform properties in all directions. It may also be designed with soft longitudinally extending side edges to aid in the comfort of a patient. The bandage 12 has a weight per unit area of at least about 5 grams per square meter. It can be used alone or it can be reinforced with organic or inorganic fillers, stitches, scrims, laminates, plastic films, or any other suitable reinforcement to obtain the desired splinting properties.

The bandage 12 is impregnated or coated with a curable resin that can be activated to form a rigid cast. The resin chemistry can be tailored to obtain the desired curing mechanism such as moisture cured, UV cured, and heat curable. It is preferred that the resin used be a moisture curable polyurethane based resin system. Two typical formulations of the reaction system is set forth in the following tables:

TABLE 1

| Isonate ↓ 143L | or | | |
|---|---|---|---|
| Mondur ↓ CD | or | polyisocyanate | 50.0% |
| Rubinate ↓ XI168 | | | |
| Pluracol ↓ P1010 | | polyol | 46.6% |
| DC-200 Silicone | | defoaming agent | 0.30% |

TABLE 1-continued

| | | |
|---|---|---|
| Benzoyl Chloride | stabilizer | 0.10% |
| Thancat. DM-70 | catalyst | 3.0% |
| | | 100% |

TABLE 2

| | | | |
|---|---|---|---|
| Isonate 143L | or | | |
| Mondur CD | or | Polysiocyanate | 50.0% |
| Carbowax PEG 600 | | | |
| Carbowax PEG 4600 | | | 22.0% |
| Carbowax PEG 8000 | | | |
| Voranol 230-238 | | | |
| Voranol 220-110 | | | 18.0% |
| Irganox 1010 | | | 2.0% |
| Antifoam 1400 | | | 4.0% |
| Methane Sulphonic Acid | | | 1.0% |
| DMDEE | | | 3.0% |
| | | | 100% |

It is desirable that the bandage 12 activates and attains rigidity sufficient to hold the fracture in position as fast as possible. The bandage 12 offers a good match with the moisture curable system as the nonwoven bandage 12 has a good level of porosity and it allows moisture to enter the whole volume of the bandage 12 and thus activate the bandage 12 quicker with a minimal amount of water.

The bandage 12 is rolled onto a core 14 for packaging. The core 14 prevents creasing of the bandage 12 and facilitates rapid, controlled, unrolling of the bandage during application.

Referring now to FIGS. 3-7, the bandage 12 is applied by removing it from the storage package 11, FIG. 1, and immersing the rolled bandage 12 in cool water of about 25 C. (77 F.), FIG. 3, the technician wearing protective gloves. Excess water is wrung from the rolled bandage 12, FIG. 4, and then immediately applied to the limb in accordance with known application techniques, FIG. 5. The applied bandage 12 is smoothed and more closely conformed to the limb while still flexible. Upon hardening, the bandage 12 is sufficiently rigid to maintain the limb in an essentially immobile position, but with enough residual softness to permit slight movement of the limb.

Figure 7:
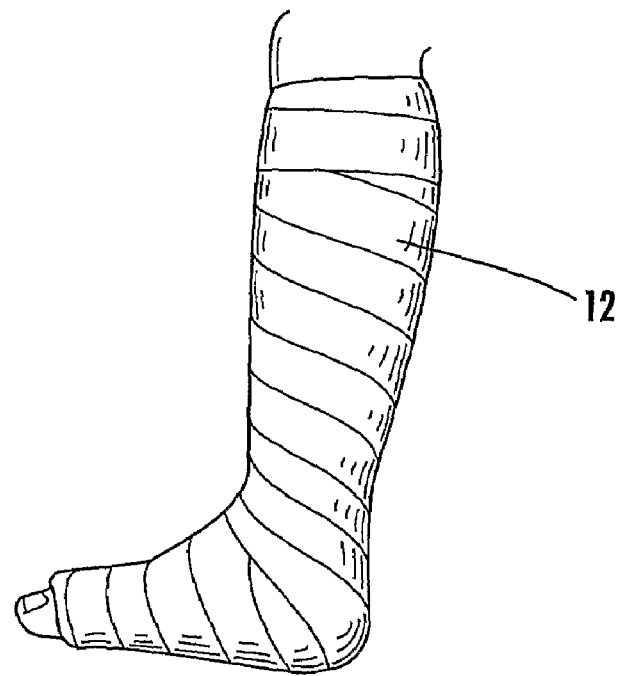
Figure 8:
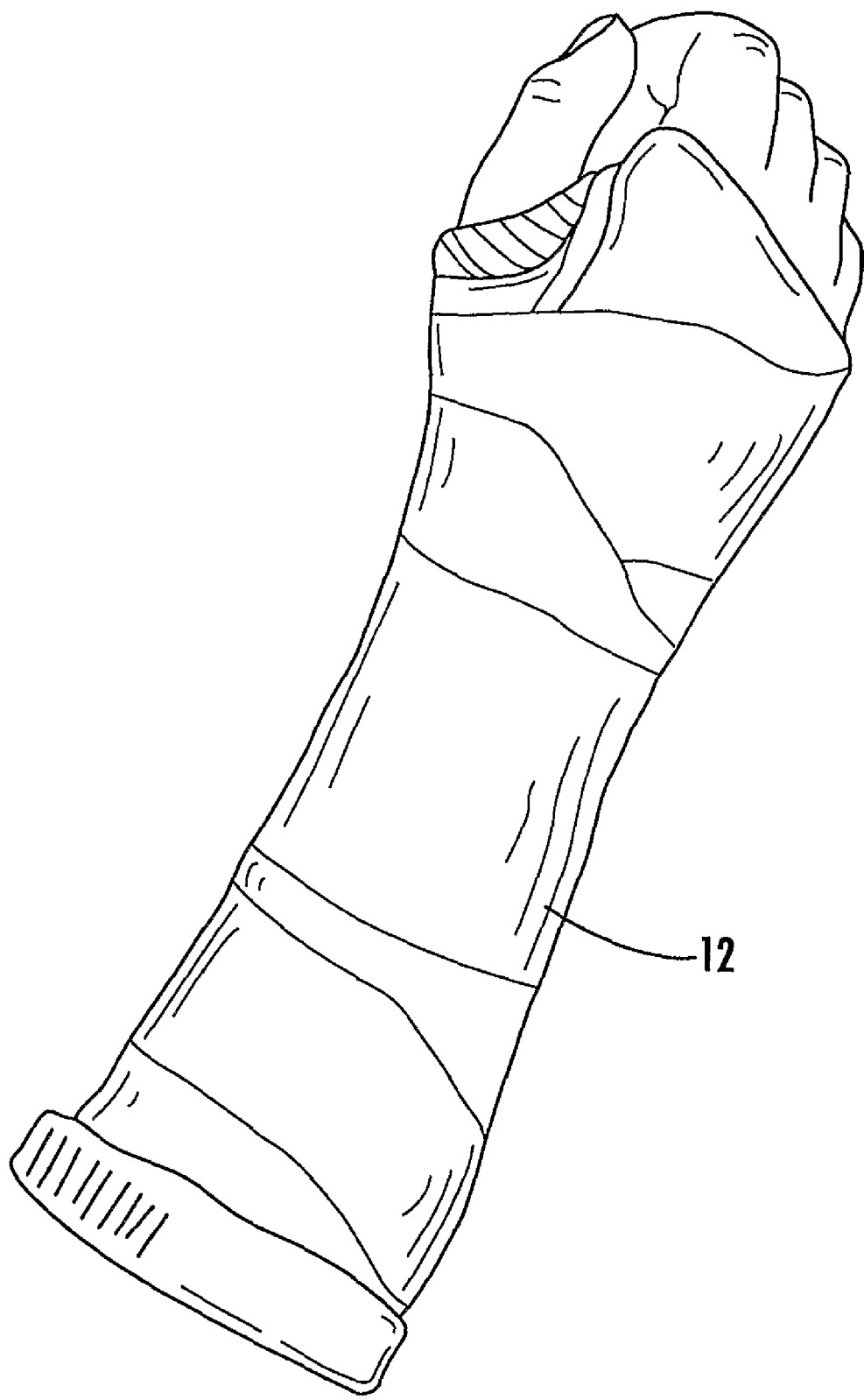
FIG. 8 is a view of the nonwoven cast bandage as applied to a forearm.

As shown in FIGS. 7 and 8, the bandage 12 can be applied to various limbs. For example, the bandage 12 can be applied to a leg, FIG. 7, or to a forearm, FIG. 8.

Splint

Figure 9:
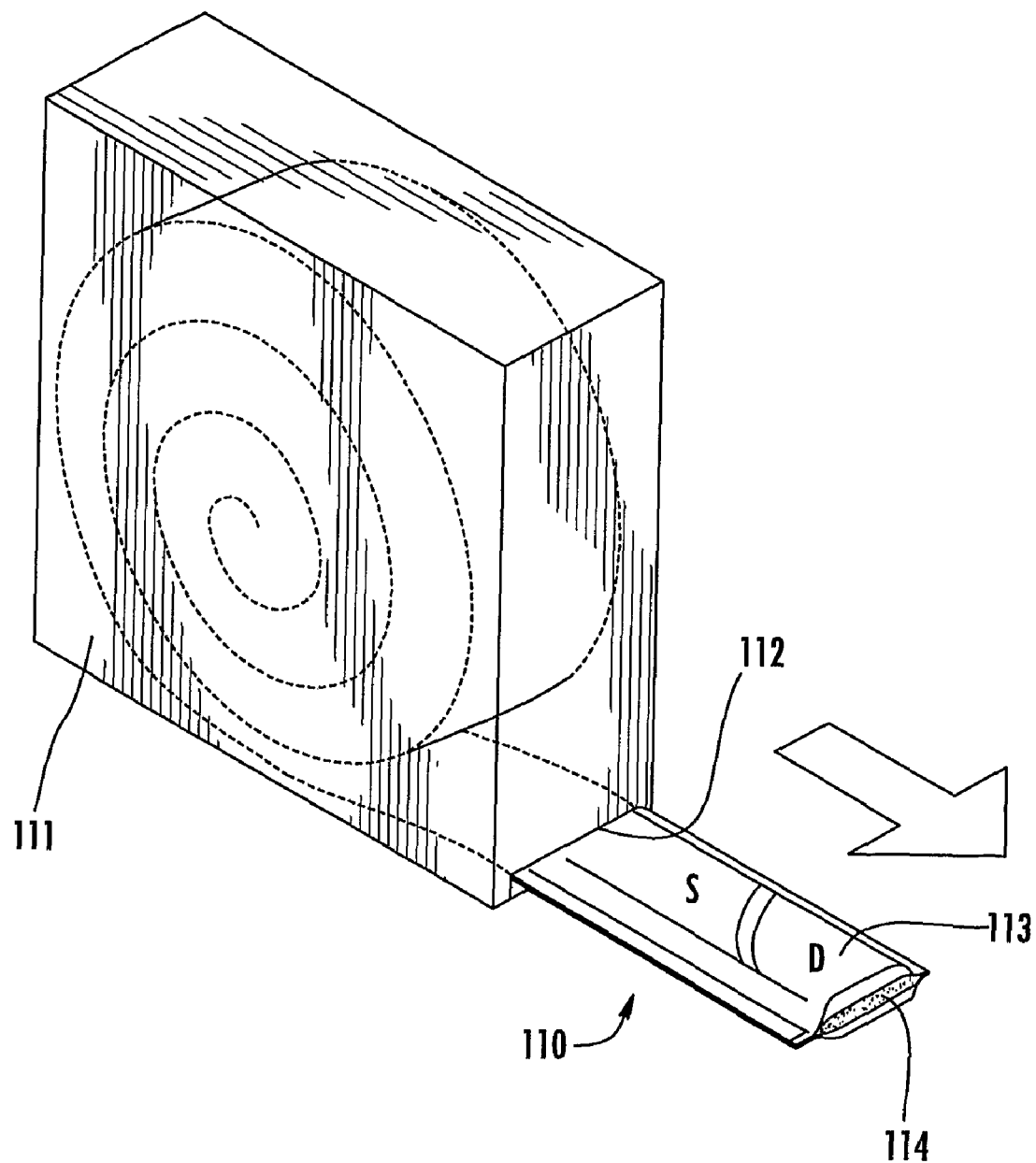
FIG. 9 is a perspective view showing a splint product according to another embodiment of the invention being dispensed from a dispenser.

A medical bandage product 110 for splinting is illustrated in FIG. 9. Bandage product 110 may be sold in any convenient length, such as 30 feet, and is rolled into a coil and positioned in a suitable dispenser 111. Dispenser carton 111 is provided with a slot 112 at one lower corner through which bandage product 110 is dispensed.

The bandage product 110 is formed of an outer elongate sleeve 113 formed of a moisture-impervious material, for example, a laminated metal foil and plastic. Sleeve 113 is heat sealed along opposite, parallel extending sides to form an elongate tube. An elongate medical bandage 114, described in detail below, is positioned within sleeve 113 and is maintained in substantially moisture-free conditions until dispensed. The bandage 114 is dispensed by pulling the needed amount of material, along with the sleeve 113 in which it is enclosed, out of the carton 111 and severing it with, for example, scissors. The remaining, raw end of the bandage 114 is tucked back into the remaining sleeve 113 with a sufficient length of sleeve available to receive a clip, such as a bar clip. Of course, any suitable form of closure may be used so long as a seal sufficient to prevent moisture intrusion is formed.

Figure 10:
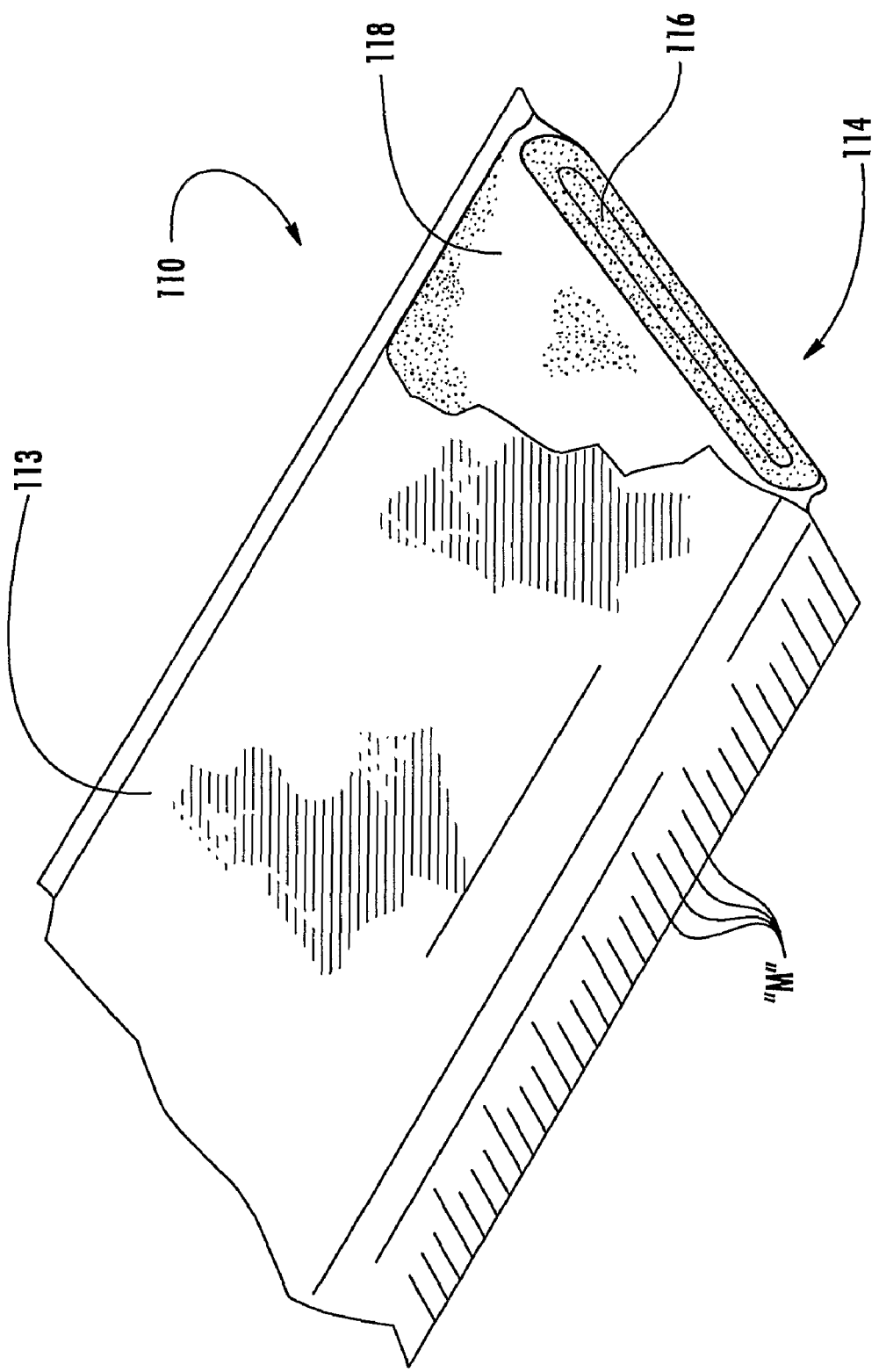
FIG. 10 is a perspective view with parts broken away of a cut length of the splint product.

Referring now to FIG. 10, since the appropriate length of bandage 114 is best determined by measurement, measurement marks "M" may be printed on one edge of the sleeve 113. The sleeve 113 is preferably closely conforming to the bandage 114 along its length in order to reduce the amount of air that is introduced into the sleeve while it is open.

Figure 11:
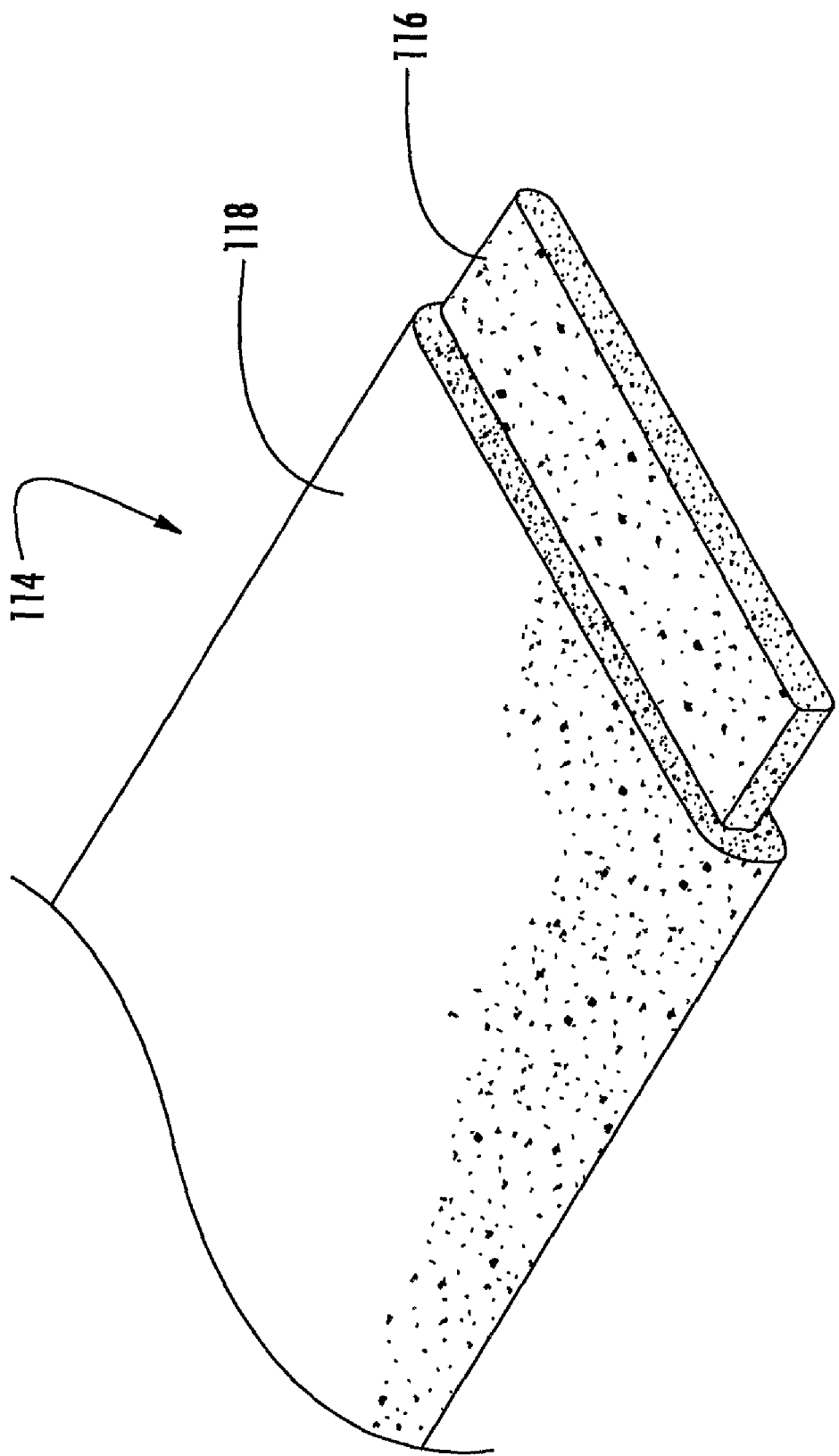
FIG. 11 is a perspective view of a length of the splint material with the nonwoven substrate layer exposed for clarity.

As shown in FIG. 11, the bandage 114 comprises a nonwoven substrate 116. Substrate 116 has a weight per unit area of at least about 50 grams per square meter, and preferably between about 200 to about 700 grams per square meter. The substrate 116 is contained within a tubular wrapping 118 that is preferably formed of a soft, flexible non-woven fiber such as polypropylene. This provides a cushioning protective layer between the skin of the patient and substrate 116.

The wrapping 118 may also be selected from a wide range of other materials such as open cell or reticulated foam, closed cell foam, soft flexible films and nonwoven materials.

Alternatively, the substrate 116 may be packed in the sleeve 113 and enclosed within a protective cushioning layer just before application. This may be accomplished by folding a length of cushioning material around the substrate 116 and securing it in place with, for example, tape or another form of adhesive.

Substrate 116 is impregnated or coated with a reactive system which remains stable when maintained in substantially moisture-free conditions but which hardens upon exposure to sufficient moisture to form a rigid, self-supporting structure. Two typical formulations of the reaction system is set forth in the following tables:

TABLE 3

| | | | |
|---|---|---|---|
| Isonate ↓ 143L | or | | |
| Mondur ↓ CD | or | polyisocyanate | 50.0% |
| Rubinate ↓ XI168 | | | |
| Pluracol ↓ P1010 | | polyol | 46.6% |
| DC-200 Silicone | | defoaming agent | 0.30% |
| Benzoyl Chloride | | stabilizer | 0.10% |
| Thancat. DM-70 | | catalyst | 3.0% |
| | | | 100% |

TABLE 4

| | | | |
|---|---|---|---|
| Isonate 143L | or | | |
| Mondur CD | or | Polysiocyanate | 50.0% |
| Carbowax PEG 600 | | | |
| Carbowax PEG 4600 | | | 22.0% |
| Carbowax PEG 8000 | | | |
| Voranol 230-238 | | | |
| Voranol 220-110 | | | 18.0% |
| Irganox 1010 | | | 2.0% |
| Antifoam 1400 | | | 4.0% |
| Methane Sulphonic Acid | | | 1.0% |
| DMDEE | | | 3.0% |
| | | | 100% |

Figure 12:
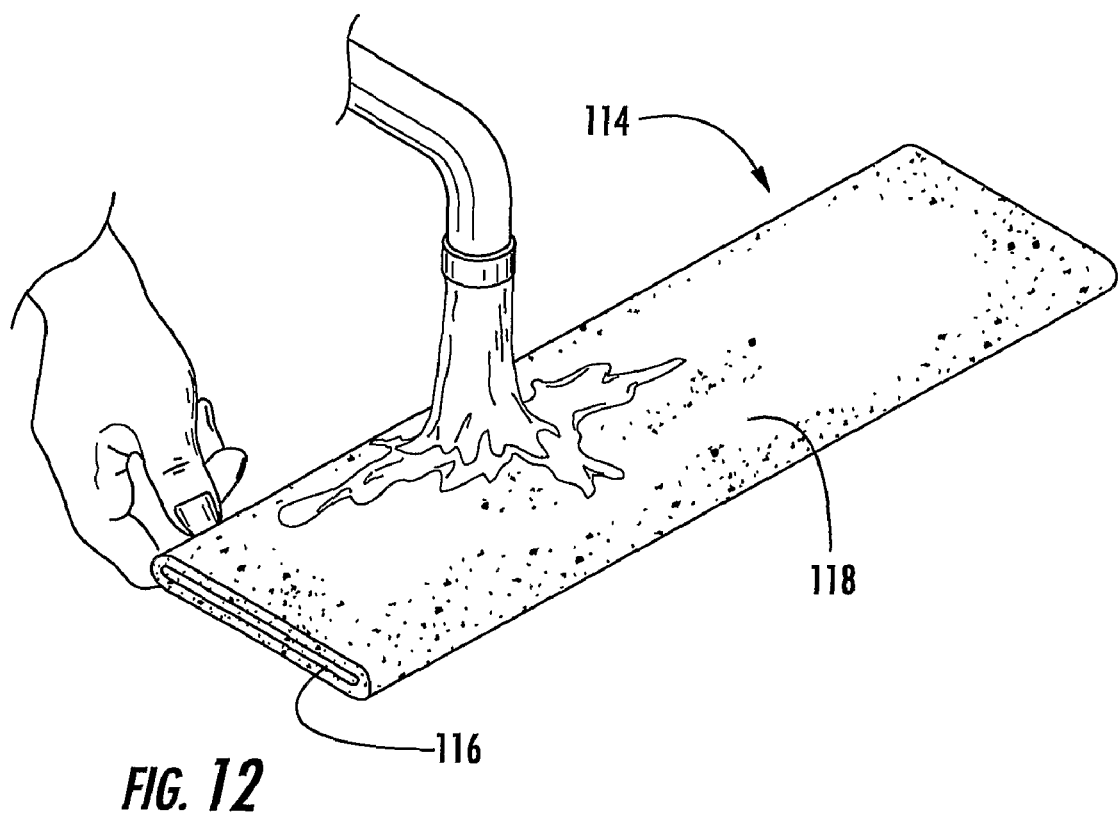
FIG. 12 illustrates activation of the moisture-curable resin in the splint material by wetting.
Figure 13:
FIG. 13 shows excess water being removed from the splint material before application.
Figure 14:
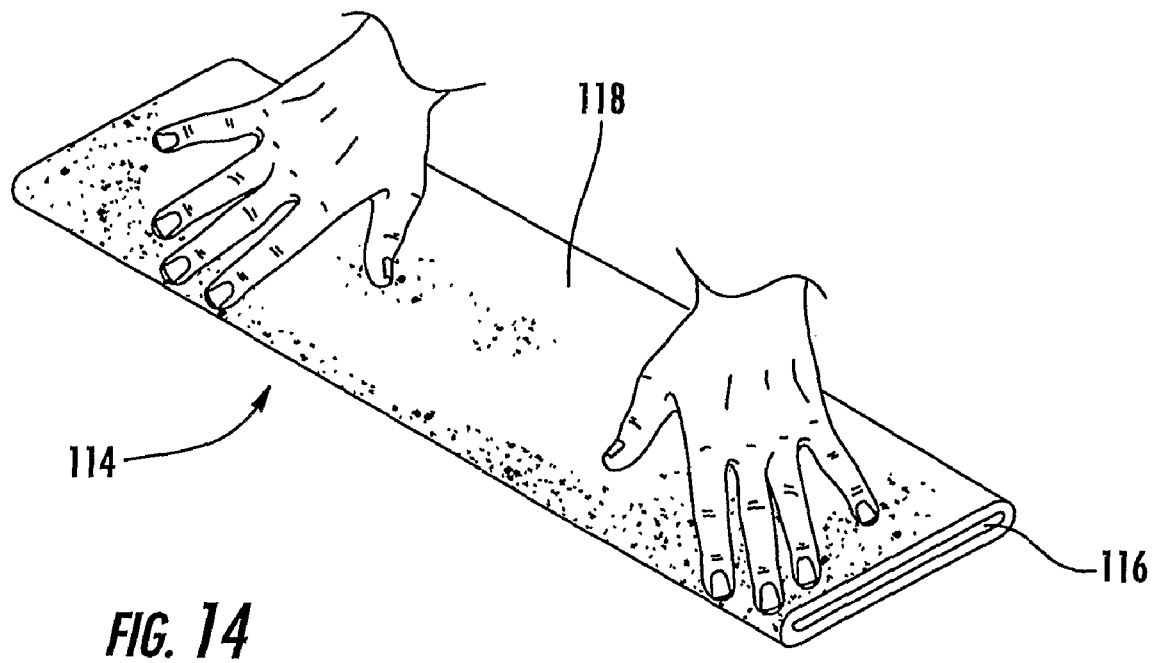
FIG. 14 shows smoothing and straightening of the splint material before application.
Figure 15:
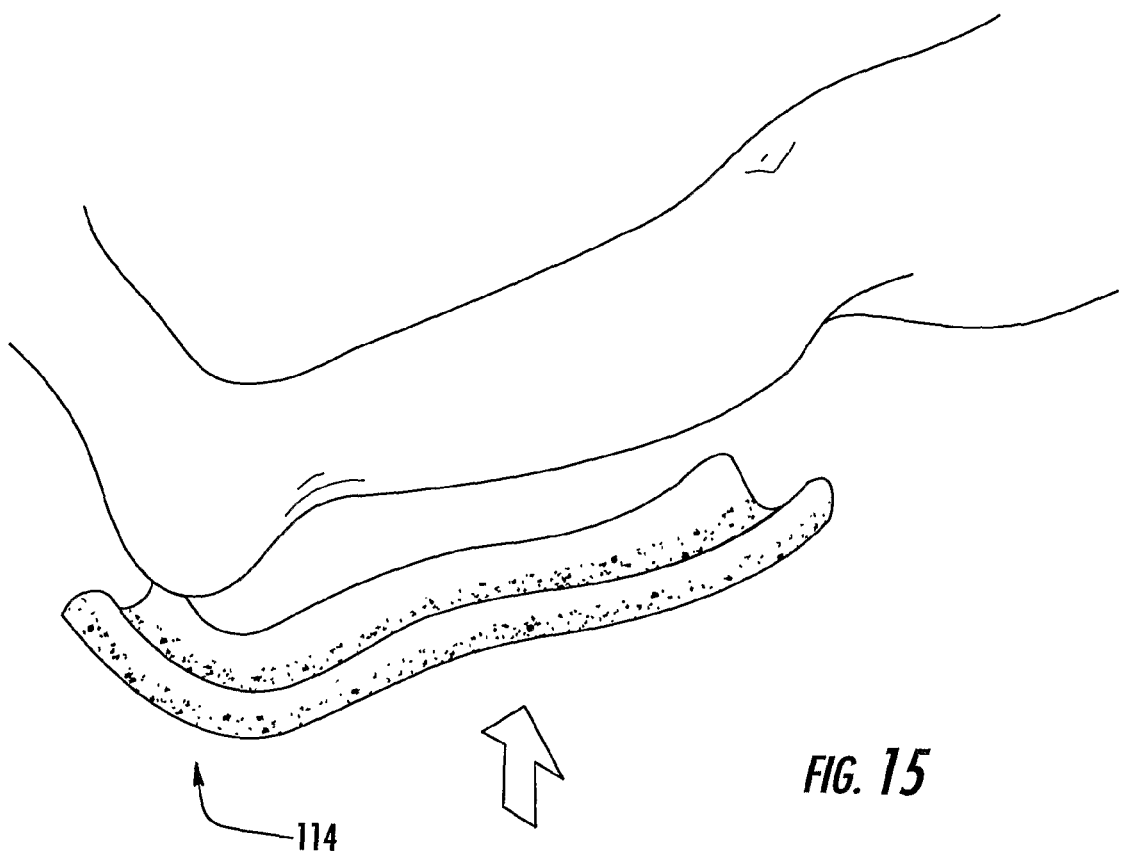
FIGS. 15 and 16 are perspective views of the splint material being placed on an injured limb and being secured into place by a covering wrap.
Figure 16:
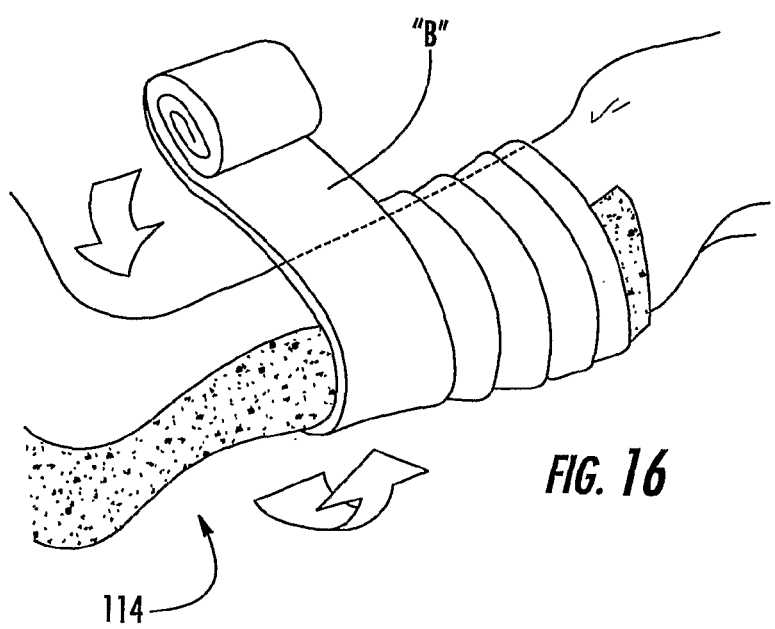

As is shown in FIGS. 12-14, the bandage 114 is typically activated by spraying or pouring water on one surface of the bandage 114, FIG. 12, wringing out the excess water, FIG. 13, and smoothing the bandage 114 before application, FIG. 14. Referring now to FIG. 15, an appropriate length of bandage 114 is formed to the shape of the body member to be immobilized. This particular type of splint, known as a posterior short leg splint, is formed by molding a length of the bandage 114 to the calf and up over the heel and onto the foot. Then, bandage 114 is overwrapped with a known elastic bandage "B", as is shown in FIG. 16.

Figure 17:
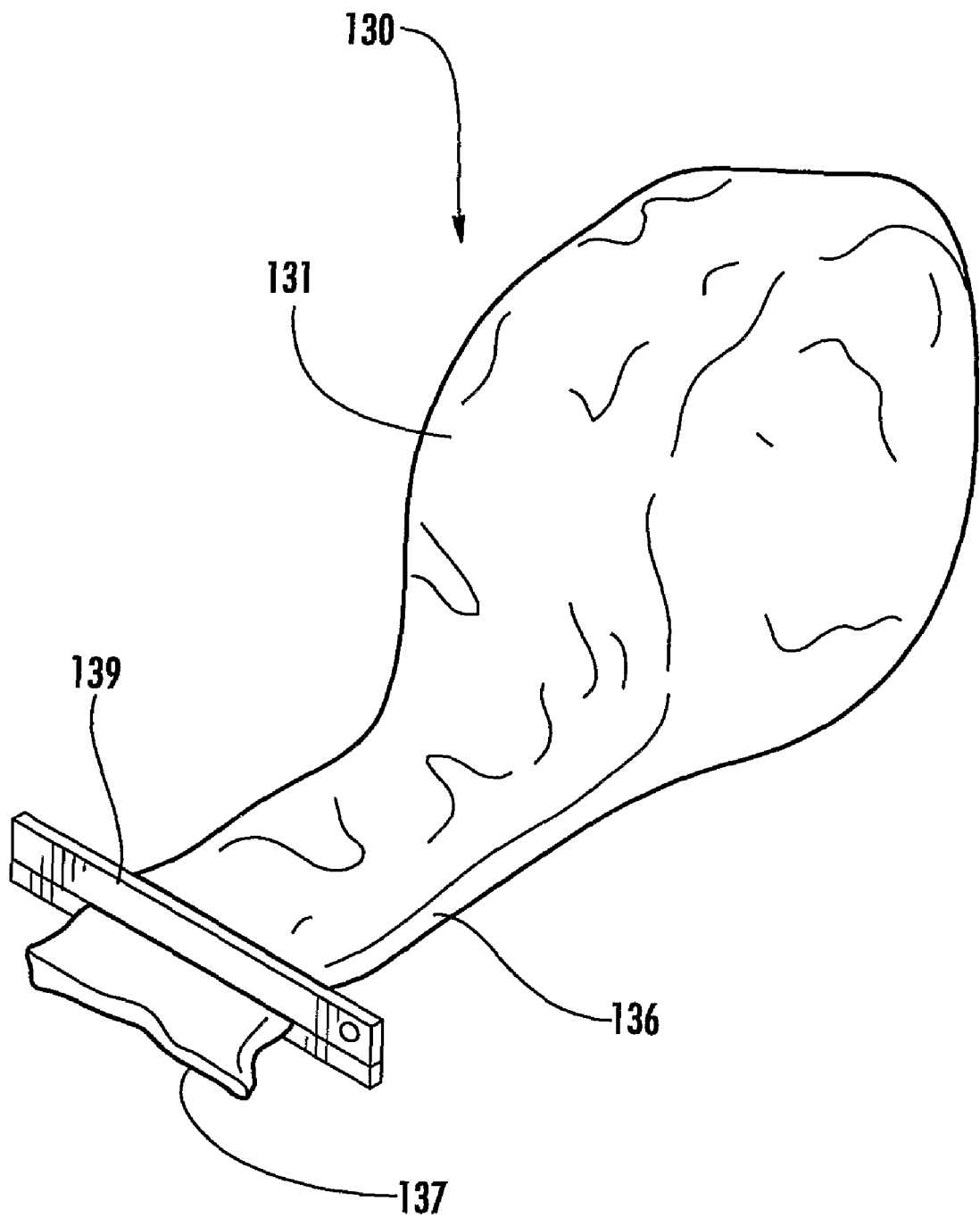
FIG. 17 is a perspective view of an alternative design of a dispensing container for holding the splint product until ready for dispensing.
Figure 18:
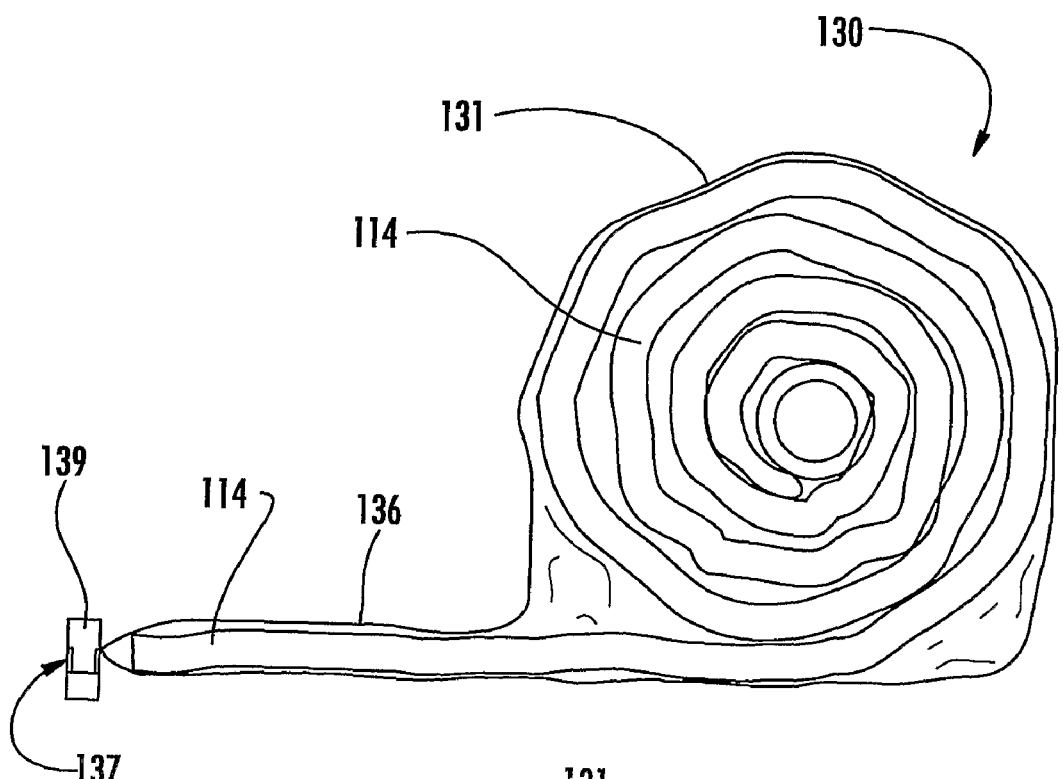
FIG. 18 is a vertical cross-section of the dispensing container shown in FIG. 18.
Figure 19:
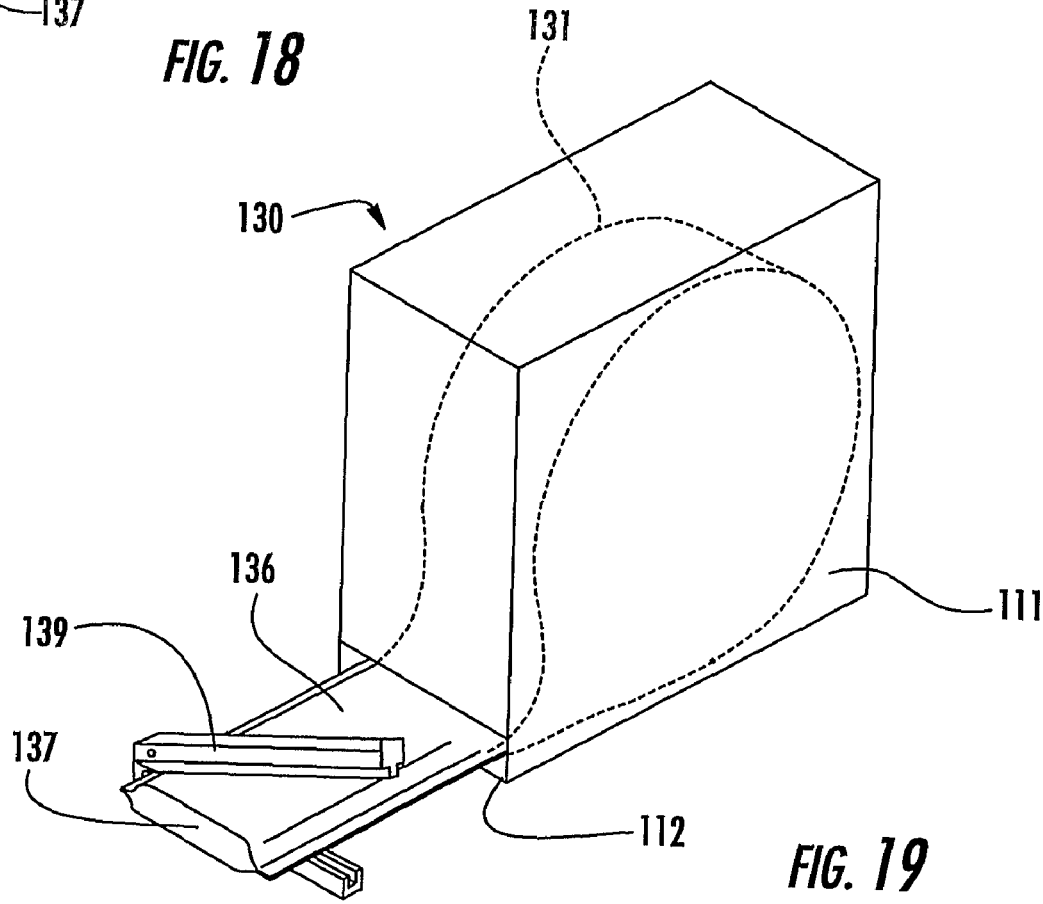
FIG. 19 is a perspective view of the dispenser carton into which the container is positioned.

Referring now to FIGS. 17-19, a medical bandaging product according to another embodiment of the invention is shown at broad reference numeral 130. The medical bandage 114 is positioned within a container 131 which is formed of two laminated elongate sheets placed in registration and heat sealed along a common seam. The outer layer is formed of a tear-resistant plastic film and the middle layer comprises aluminum foil and acts as a moisture barrier. The inner layer is a plastic film having thermoplastic properties suitable for heat sealing the interior of container 131 securely against moisture.

As is also shown in FIG. 17, container 131 includes an elongate dispensing sleeve 136 having an openable end 137 through which the medical bandage 114 in the container 131 is dispensed.

As is shown in FIGS. 18 and 19, the end 137 of dispensing sleeve 136 may be sealed with a clamp of any suitable type, such as a bar clamp 139.

As is shown in FIG. 18, dispensing sleeve 136 fits snugly around the medical material 114 in order to limit exposure of the medical material 114 to air which enters when the opening 137 is unsealed for dispensing the medical bandage 114. FIG. 18 also shows that the medical material 114 is coiled into a relatively tight coil to limit exposure to air and sealed into the container 131. When opening 137 is properly sealed, container 131 is sufficiently airtight so that medical material 114 remains in its' soft, uncured state for much longer than the usual length of time needed to exhaust the supply of medical bandage 114 in container 131. If a short length of the medical bandage 114 adjacent the opening 137 hardens, it can be cut away and discarded.

A desired length of medical bandage 114 is dispensed by removing clamp 139 and grasping the exposed end of the medical bandage 114. The appropriate length is pulled out of container 131 causing the medical bandage 114 to uncoil in the container 131. When the proper length has been dispensed through opening 137, it is cut and the end is tucked back into the dispensing sleeve 136. The open end 137 is quickly resealed.

Figure 20:
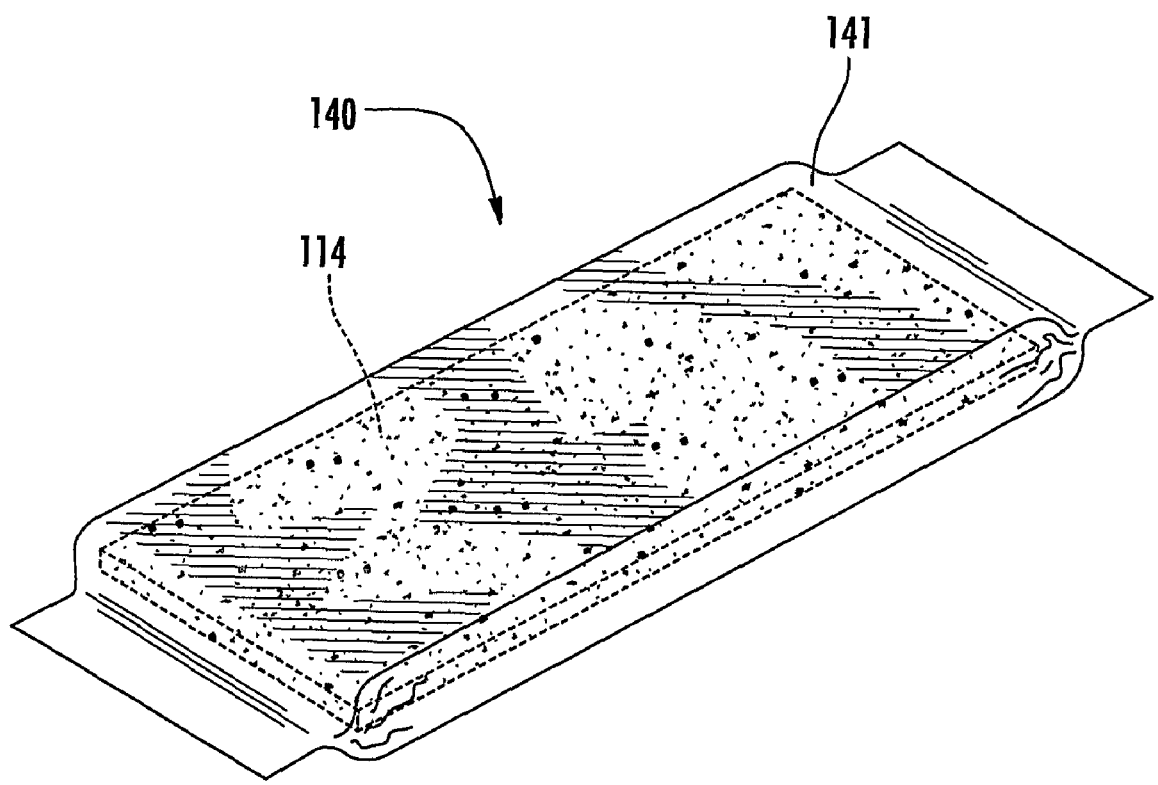
FIG. 20 is a perspective view of a pre-cut splint product stored for use in a moisture-impervious envelope until ready for use.

Referring now to FIG. 20, a pre-cut embodiment of a medical bandage product 140 is shown. The medical bandage product 140 comprises a moistureimpervious envelope 141 in which is packaged a pre-cut length of the medical bandage 114. The medical bandage 114 is sized according to the desired end use and is labeled as such. The medical bandage 114 may be removed from the envelope 141 and used as is, or cut and shaped as needed to meet the medical requirements of the treating physician and technician.

By way of a further alternative, the resin-coated or impregnated substrate 116 may be packaged in the sleeve 113 without a tubular wrapping. The substrate is removed from the sleeve 113, wetted, positioned within a protective wrapping of the user's choice, and then applied to the patient. Wringing to remove any excess water may be carried out, if necessary, either before or after application of the wrapping to the substrate 116. To facilitate application of the wrapping, the wrapping may be in the form of a flat sheet of cushion material of sufficient width to extend around the substrate 116 to form a tubular enclosure. The cushion material may be held in its tubular condition around the substrate by, for example, double-sided adhesive tape in a manner similar to that shown in applicant's U.S. Pat. No. 6,719,710, particularly FIG. 14.

Medical bandage products are described above. Various details of the invention may be changed without departing from its scope. Furthermore, the foregoing description of the preferred embodiments of the invention and the best mode for practicing the invention are provided for the purpose of illustration only and not for the purpose of limitation.

We claim:

1. A medical bandaging product, comprising:
   (a) a non-woven, fibrous, flexible medical material consisting essentially of a cast tape having a weight of about 5 grams per square meter and adapted for being applied and conformed to a body part to be supported;
   (b) a reactive system impregnated into or coated onto the medical material, the system remaining stable when maintained in a non-activated condition in the absence of an activating agent, and hardening upon activation by exposure to the activating agent to form a rigid, self supporting structure; and
   (c) an enclosure within which the medical material is maintained against exposure to the activating agent until use.

2. A medical bandaging product according to claim 1, wherein the medical material comprises a cast tape, the reactive system comprises a reactive system that remains stable when maintained in substantially moisture-free conditions and hardens upon exposure to sufficient moisture to form a rigid, self supporting structure, and the activating agent comprises moisture.

3. A medical bandaging product according to claim 2, wherein the medical material is in a rolled configuration, and wherein the enclosure comprises an envelope.

4. A medical bandaging product according to claim 1., wherein the non-woven fibrous medical material is foil led from fibers selected from the group consisting of glass, polyester, polypropylene and blends thereof.

5. A medical bandaging product according to claim 1, 2 or 4, wherein the medical material is formed by a non-woven process selected from the group consisting of spray bonding, spun bonding, needle punching, felting, spun lacing, and stitch bonding.

6. A medical bandaging product according to claim 1, wherein the non-woven medical material includes a reinforcement element selected from the group consisting of an inorganic filler, stitches, scrim, laminate, and plastic film.

7. A medical bandaging product according to claim 1, wherein the non-woven medical material comprises a plurality of stitches that provides increased rigidity when the material has hardened into the rigid, self supporting structure.

8. A medical bandaging product according to claim 1, wherein the non-woven medical material comprises a reinforcing laminate material that provides increased. rigidity when the material has hardened into the rigid, self supporting structure.

9. A medical bandaging product according to claim 1, wherein the non-woven medical material comprises a reinforcing plastic film that provides increased rigidity when the material has hardened into the rigid, self supporting structure.

* * * * *

UNITED STATES PATENT AND TRADEMARK OFFICE
CERTIFICATE OF CORRECTION

PATENT NO. : 8,343,082 B2
APPLICATION NO. : 11/916341
DATED : January 1, 2013
INVENTOR(S) : John C. Evans, Shitij Chabba and Martin O'Hara It is certified that error appears in the above-identified patent and that said Letters Patent is hereby corrected as shown below:

Column 8, line 36, delete "foil led" and enter --formed--.

Signed and Sealed this
Nineteenth Day of February, 2013

Teresa Stanek Rea
*Acting Director of the United States Patent and Trademark Office*